(12) United States Patent
Shinozaki et al.

(10) Patent No.: US 6,344,452 B1
(45) Date of Patent: Feb. 5, 2002

(54) 1,5-BENZODIAZEPINE DERIVATIVES

(75) Inventors: Katsuo Shinozaki; Tomoyuki Yoneta; Masakazu Murata; Naoyoshi Miura; Kiyoto Maeda, all of Saitama (JP)

(73) Assignee: Zeria Pharmaceuticals Co., Ltd., Tokyo (JP)

( * ) Notice: Subject to any disclaimer, the term of this patent is extended or adjusted under 35 U.S.C. 154(b) by 0 days.

(21) Appl. No.: 09/701,562

(22) PCT Filed: Aug. 29, 1999

(86) PCT No.: PCT/JP99/02835

§ 371 Date: Dec. 5, 2000

§ 102(e) Date: Dec. 5, 2000

(87) PCT Pub. No.: WO99/64403

PCT Pub. Date: Dec. 16, 1999

(30) Foreign Application Priority Data

Jun. 5, 1998 (JP) ............................................ 10-172127

(51) Int. Cl.$^7$ .................. C07D 243/12; A61K 31/5513; A61P 1/06; A61P 25/14

(52) U.S. Cl. ....................................... 514/221; 540/517

(58) Field of Search ........................... 514/221; 540/517

(56) References Cited

U.S. PATENT DOCUMENTS 6,239,131 B1 * 5/2001 Shinozaki et al. .......... 514/221

FOREIGN PATENT DOCUMENTS

| WO | WO 94/24151 | 10/1994 |
| WO | WO 94/25444 | 11/1994 |
| WO | WO 95/18110 | 7/1995 |
| WO | WO 96/40656 | 12/1996 |
| WO | WO 98/25911 | 6/1998 |

OTHER PUBLICATIONS

G. Currutto, et al., Tetrahedron, vol. 53, No. 21, pp. 7347–7364, "A Chemical Method for the Preparation of Novel 1,5–Benzodiazepines Acting as CCK–B Antagonists in High Enantiometric Purity," 1997.

G.C. Hist, et al., J. Med. Chem., vol. 30, pp. 5236–5245, "Discovery of 1,5–Benzodiazepines with Peripheral Cholecystokinin (CCK–A) Receptor Agonist Activity (II): Optimization of the C3 Amino Substituent," 1996.

C.J. Aquino, et al., J. Med. Chem., vol. 39, No. 2, pp. 562–569, "Discovery of 1,5–Benzodiazepines with Peripheral Cholecystokinin (CCK–A) Receptor Agonist Activity Optimization of the Agonist 'Trigger'," 1996.

* cited by examiner

*Primary Examiner*—Bruck Kifle
(74) *Attorney, Agent, or Firm*—Oblon, Spivak, McClelland, Maier & Neustadt, P.C.

(57) ABSTRACT

This invention relates to 1,5-benzodiazepine derivatives, which are each represented by the following formula (1):

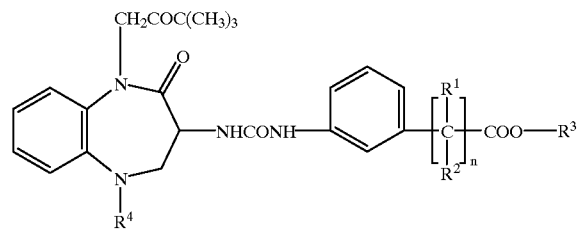

(1)

wherein $R^1$ represents a lower alkyl group, $R^2$ and $R^3$ may be the same or different and represent a hydrogen atom or a lower alkyl group, $R^4$ represents a cyclohexyl group or phenyl group, and n stands for an integer of from 1 to 3, and also to medicines containing the same. These compounds are useful as curatives or preventives for diseases in which a gastrin receptor and/or a CCK-B receptor takes part.

4 Claims, No Drawings

1,5-BENZODIAZEPINE DERIVATIVES

TECHNICAL FIELD

This present invention relates to benzodiazepine derivatives, which are important in the medical field. Specifically, the present invention is concerned with novel 1,5-benzodiazepine derivatives, which antagonize gastrin receptors and/or CCK-B (cholecystokinin-B) receptors, and also with medicines for preventing and/or treating diseases in which the receptors take part.

BACKGROUND ART

Cholecystokinin (CCK) is a gastrointestinal hormone produced at and released from the duodenal and jejunal mucosas, and is known to have actions such as pancreatic juice secretion stimulation, gallbladder contraction stimulation and insulin secretion stimulation. Further, CCK is also known to exist at high concentrations in the cerebral cortex, the hypothalamus and the hippocampus, and is also known to have actions such as suppressing food intake, enhancing memory, generating anxiety and the like. On the other hand, gastrin is a gastrointestinal hormone produced at and released from G cells which are distributed in the pylorus, and is known to have effects such as gastric acid secretion stimulation, pylorus contraction stimulation and gallbladder contraction stimulation.

These CCK and gastrin have the same five C-terminal amino acids, and both exhibit their effects via receptors. CCK receptors are classified into peripheral CCK-As distributed in the pancreas, the gallbladder, the intestinal tract and the like and central CCK-Bs distributed in the brain. Gastrin receptors and CCK-Bs show similar properties in receptor binding experiments and have high homology, so that they may be called "CCK-Bs/gastrin receptors". Antagonistic compounds to these receptors, for example, gastrin receptors or CCK-B receptors can be used for the treatment and/or prevention of gastric ulcer, duodenal ulcer, gastritis, reflux esophagitis, pancreatitis, Zollinger-Ellison syndrome, vacuolating G cell hyperplasia, basal mucosa hyperplasia, cholecystitis, biliary colic, gastrointestinal dysmotility, irritable bowel syndrome, certain types of tumors, eating disorder, anxiety, panic disorder, depression, schizophrenia, parkinsonism, tardive dyskinesia, Gilles de la Tourette's syndrome, drug dependance, and drug-withdrawal symptoms. They are also expected to have effects such as induction of ataralgesia and enhancement of ataralgesia induction by opioid drugs [Folia Pharmacologica Japonica, 106, 171–180 (1995); Drugs of the Future, 18, 919–931 (1993); American Journal of Physiology, 269, G628-G646 (1995); American Journal of Physiology, 259, G184–190 (1990); European Journal of Pharmacology, 261, 257–263 (1994); Trends in Pharmacological Science, 15, 65–66 (1994)].

As a gastrin receptor antagonist, proglumide is already known as a remedy for gastric ulcer and gastritis. However, proglumide has considerably low affinity to gastrin receptors or CCK-B receptors, and has a low curative effect. Further, some benzodiazepine derivatives such as L-365,718 (devazepide, Japanese Patent Application Laid-Open (Kokai) No.63666/1986) and L-365,260 (Japanese Patent Application Laid-Open (Kokai) No. 238069/1988) have been reported to exhibit CCK-A receptor antagonism and CCK-B receptor antagonism. In addition, it is disclosed that compounds having strong CCK-B antagonism inhibit pentagastrin-stimulated acid secretion (WO 94/438, WO 95/18110). These compounds are, however, not fully satisfactory when administered in vivo. Accordingly, clinically-applicable gastrin receptor or CCK-B receptor antagonists have not been provided yet.

Compounds which can strongly bind to gastrin receptors or CCK-B receptors are useful for the prevention and/or treatment of diseases in which the respective receptors take part in the alimentary tract and the central nervous system. There is hence an outstanding desire for such compounds.

DISCLOSURE OF THE INVENTION

Under such circumstances, the present inventors have proceeded with an extensive investigation to solve the above-described problems. As a result, it was found that 1,5-benzodiazepine derivatives having a specific structure have strong gastrin receptor and/or CCK-B receptor antagonism and achieve strong inhibition of acid secretion and are useful as medicines for the prevention and/or treatment of diseases in which these receptors take part, and an application for patent has already been filed (PCT/JP97/04534). The present inventors have proceeded with further research. As a result, it has been found that 1,5-benzodiazepine derivatives each of which contains a branched fatty acid group achieve still better inhibition of pentagastrin-stimulated acid secretion in rats and inhibition of pentagastrin-stimulated acid secretion in beagles with Heidenhain pouch, leading to the completion of the present invention.

Therefore, the present invention provides a 1,5-benzodiazepine derivative represented by the following formula (1):

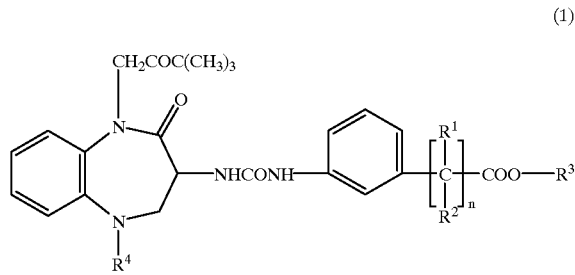

(1)

wherein $R^1$ represents a lower alkyl group, $R^2$ and $R^3$ may be the same or different and represent a hydrogen atom or a lower alkyl group, $R^4$ represents a cyclohexyl group or phenyl group, and n stands for an integer of from 1 to 3; or a salt thereof.

The present invention also provides a medicament comprising as an effective ingredient the 1,5-benzodiazepine derivative (1) or the salt thereof.

The present invention also provides a medicinal composition comprising the 1,5-benzodiazepine derivative (1) or the salt thereof and a pharmaceutically acceptable carrier.

The present invention also provides the 1,5-benzo-diazepine derivative (1) or the salt thereof as a medicament.

The present invention further provides a treatment method of a disease in which a gastrin receptor and/or a CCK-B receptor takes part, which comprises administering the 1,5-benzo-diazepine derivative (1) or the salt thereof.

BEST MODES FOR CARRYING OUT THE INVENTION

The term "lower" as used herein means a linear or branched carbon chain having a carbon number of from 1 to 8.

Therefore, examples of the lower alkyl groups represented by $R^1$, $R^2$ and $R^3$ in the formula (1) can include methyl, ethyl, propyl, isopropyl, butyl, isobutyl, sec-butyl, tert-butyl, pentyl, 1-methylbutyl, 2-methylbutyl, isopentyl, tert-pentyl, 1,2-dimethylpropyl, neopentyl, 1-ethylpropyl, hexyl, 1-methylpentyl, 2-methylpentyl, 3-methylpentyl, isohexyl, 1-ethylbutyl, 2-ethylbutyl, 1,1-dimethylbutyl, 1,2-dimethyl-butyl, 1,3-dimethylbutyl, 2,2-dimethylbutyl, 2,3-dimethyl-butyl, 3,3-dimethylbutyl, 1-methyl-1-ethylpropyl, 1-ethyl-2-methylpropyl, 1,1,2-trimethylpropyl, 1,2,2-trimethylpropyl, heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylbutyl, 1-methylheptyl, 2-methylheptyl, 3-methylheptyl, 4-methylheptyl, 5-methylheptyl, 6-methyl-heptyl, 1-ethylhexyl, 2-ethylhexyl, 3-ethylhexyl, 4-ethyl-hexyl, 1-propylpentyl, 2-propylpentyl, 3,3,4-trimethylpentyl, 3,4,4-trimethylpentyl, 1,1,2,2-tetramethylbutyl, 2,2,3,3-tetramethylbutyl, and 1,1,3,3-tetramethylbutyl. Among these, alkyl groups the carbon numbers of which range from 1 to 4 are preferred, with methyl being particularly preferred.

Compounds of the formula (1) in which $R^1$ and $R^2$ are methyl groups, n is 1 and $R^3$ is a hydrogen atom, that is, of the following formula (1a) are particularly preferred:

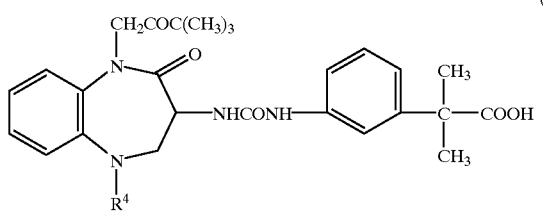
(1a)

wherein $R^4$ represents the same as defined above.

Illustrative of the salt of the compound (1) according to the present invention are acid addition salts with inorganic acids, such as the hydrochloride, the sulfate, the nitrate and the hydroiodate; acid addition salts with organic acids, such as the methanesulfonate and the ethanesulfonate; inorganic salts such as the sodium salt, the potassium salt, the calcium salt and the magnesium salt; and organic salts such as the ammonium salt, the pyridine salt, the triethylamine salt, the ethanolamine salt, the trans-4-aminocyclohexanol salt and the N,N'-dibenzylethylenediamine salt. Among these, the sodium salt, the trans-4-aminocyclohexanol salt and the N,N'-dibenzyl-ethylenediamine salt are particularly preferred.

In the present invention, the compounds (1) of the present invention and also various solvates of the compounds (1), such as their hydrates, and polymorphic substances are included. Further, racemic modifications, various diastereomers, diastereomer mixtures and optically active substances of the compounds (1) according to the present invention are all encompassed. Among these, the optically active substances are particularly preferred.

The compounds (1) of the present invention can be produced by applying various synthesis processes in view of characteristics of their fundamental structure and groups. Some representative production processes will be described hereinafter.

Production Process A

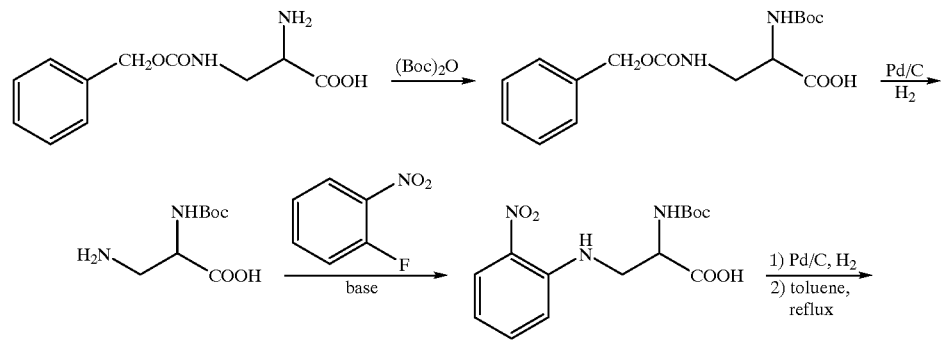

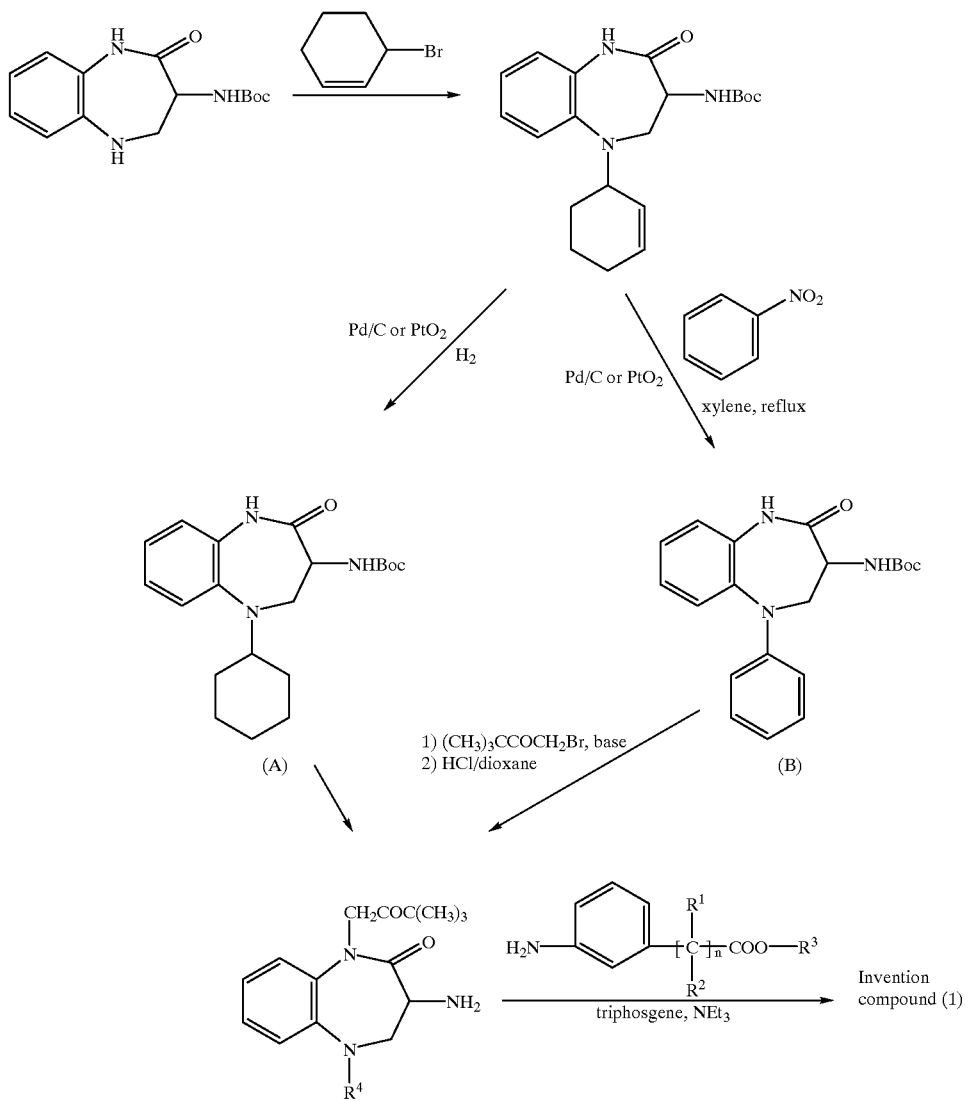

wherein Boc represents a tert-butoxycarbonyl group, and $R^1$, $R^2$, $R^3$, $R^4$ and n represent the same as defined above.

Described specifically, di-tert-butyl dicarbonate is reacted with 2-amino-3-benzyloxycarbonylaminopropionic acid to obtain 2-tert-butoxycarbonylamino-3-benzyloxycarbonyl-aminopropion ic acid, followed by its debenzylation into 3-amino-2-tert-butoxycarbonylaminopropionic acid in the presence of a catalyst of palladium carbon and hydrogen. In the presence of a base such as potassium carbonate, 2-fluoronitrobenzene is reacted with 3-amino-2-tert-butoxycarbonylaminopropionic acid to obtain 2-tert-butoxycarbonylamino-3-(2-nitrophenyl)aminopropionic acid. This is subjected to catalytic reduction in the presence of a catalyst of palladium carbon, followed by refluxing under heat in toluene, whereby 2-oxo-3-tert-butoxycarbonylamino-1,3,4,5-tetrahydro-2H-1,5-benzodiazepine is obtained. With this compound, 3-bromocyclohexene is reacted to obtain 2-oxo-3-tert-butoxycarbonylamino-5-(2-cyclohexen-1-yl)-1,3, 4,5-tetrahydro-2H-1,5-benzodiazepine. Hydrogenation of this compound in the presence of a catalyst of palladium carbon or platinum oxide provides the compound (A). On the other hand, dehydrogenation of 2-oxo-3-tert-butoxycarbonylamino-5-(2-cyclohexen-1-yl)-1,3,4,5-tetrahydro-2H-1,5-benzodiazep ine in the presence of nitrobenzene and a catalyst of palladium carbon or platinum oxide provides the compound (B). When bromomethyl tert-butyl ketone is reacted with the compound (A) or (B) in the presence of a base such as potassium carbonate and deprotection is then conducted by treatment with hydrochloric acid or the like, 1-tert-butylcarbonylmethyl-2-oxo-3-amino-5-cyclohexyl(or phenyl)-1,3,4,5-tetrahydro-2H-1,5-benzodiazepine is obtained. By reacting triphosgene and a 3-aminophenyl branched fatty acid with this compound in the presence of a base such as triethylamine, the compound (1) of the present invention can be obtained.

Production Process B

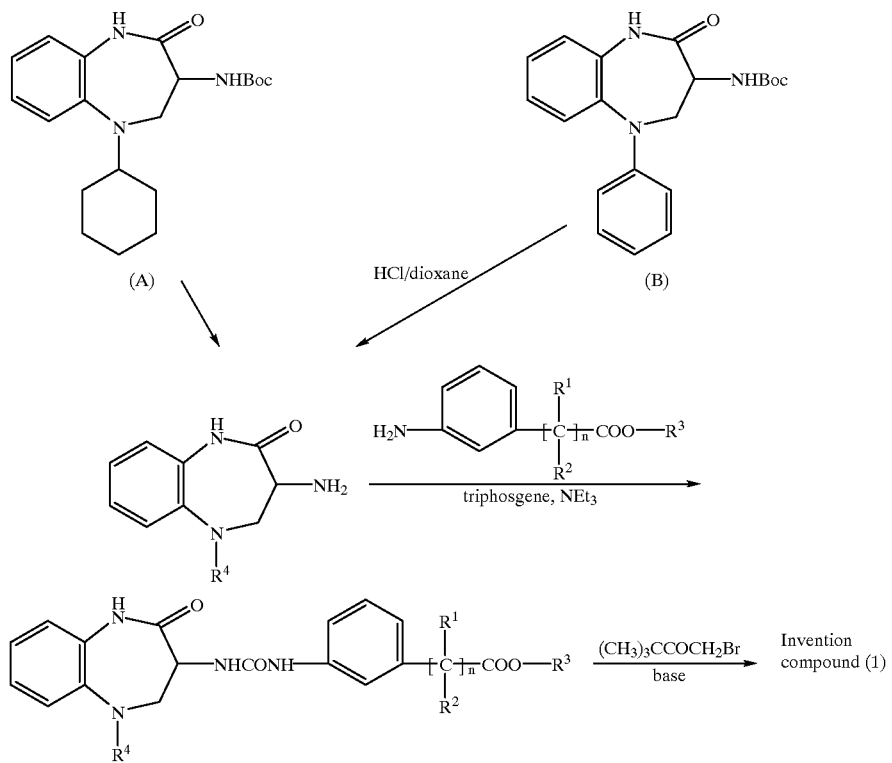

wherein Boc, $R^1$, $R^2$, $R^3$, R4 and n represent the same meanings as defined above.

Described specifically, subsequent to deprotection of the compound (A) or compound (B) through a reaction with hydrochloric acid or the like, triphosgene and a 3-aminophenyl branched fatty acid are reacted in the presence of a base such as triethylamine, whereby a ureido derivative is obtained. By reacting bromomethyl tert-butyl ketone with the ureido derivative in the presence of a base such as potassium carbonate, the compound (1) of the present invention is obtained.

When $R^3$ is a lower alkyl group, subsequent hydrolysis with an acid or a base by a method known per se in the art makes it possible to convert the compound (1) of the present invention into another compound (1) of the present invention in which $R^3$ is a hydrogen atom.

The compound (1) produced as described above is isolated either in a free form or as a salt, and is then purified. The isolation and purification are conducted by suitably choosing usual procedures such as extraction, concentration, distillation, crystallization, filtration, recrystallization, trituration and chromatography. Further, the compound (1) of this invention, which has been isolated and purified in the free form, can be converted into a salt with an acid or base by mixing it with the acid or base and then conducting its dissolution or the like under heat in a manner known per se in the art. Moreover, a chiral isomer of the compound (1) according to the present invention can be produced by using a suitable starting material compound. It can also be produced by general racemic resolution, for example, by converting the compound (1) of the present invention into a diastereomer salt with a general chiral acid such as dibenzoyl tartrate and then subjecting the diastereomer salt to optical resolutionorby converting it into a diastereomer compound, isolating it and then subjecting the same to Edman degradation.

The compound (1) according to the present invention or its salt can be administered either orally or parenterally. As oral dosage forms, the compound of the present invention can be formed into solid pharmaceutical preparations such as tablets, powders and capsules by suitably combining it with pharmaceutically acceptable carriers, for example, excipients such as lactose, mannitol, corn starch and crystalline cellulose; binders such as cellulose derivatives, acacia and gelatin; disintegrants such as carboxymethylcellulose calcium; and lubricants such as talc and magnesium stearate. It can also be formed into liquid pharmaceutical preparations such as liquid preparations, suspensions and emulsions.

As parenteral dosage forms, it can be formed into liquid preparations for injection, for example, by combining it with water, ethanol, glycerin and the like.

The dose of the compound (1) according to the present invention or the salt thereof, which is required to effectively treat or prevent the above-describe diseases, varies depending on the pharmaceutical preparation form, the administration route, the age and the conditions. In general, however, a daily oral dose to an adult may range from 1 to 1,000 mg, preferably from 5 to 500 mg. As an administration method, it is preferred to administer the dose once a day or in about 2 to 3 portions in a day.

As the compound (1) of the present invention or the salt thereof has strong gastrin receptor and/or CCK-B receptor antagonism and strong acid secretion inhibiting action as will be described subsequently herein, it is useful for treating, improving and/or preventing diseases in which gastrin receptors and/or CCK-B receptors take part, for example, gastric ulcer, duodenal ulcer, gastritis, reflux esophagitis, pancreatitis, Zollinger-Ellison syndrome, vacuolating G cell hyperplasia, basal mucosa hyperplasia, cholecystitis, biliary colic, gastrointestinal dysmotility, irritable bowel syndrome, certain types of tumors, eating disorder, anxiety, panic disorder, depression, schizophrenia, parkinsonism, tardive dyskinesia, Gilles de la Tourette's syndrome, drug dependance, and drug-withdrawal symptoms, and also for inducing ataralgesia and enhancing ataralgesia induction by opioid drugs.

EXAMPLES

The present invention will next be described in detail by examples, which should not be construed as limiting the invention thereto.

Example 1

Preparation of (±)-2-[3-[3-(1-tert-butylcarbonylmethyl-2-oxo-5-cyclohexyl-1,3,4,5-tetrahydro-2H-1,5-benzodiazepin-3-yl)ureido]phenyl]-2-methylpropionic acid

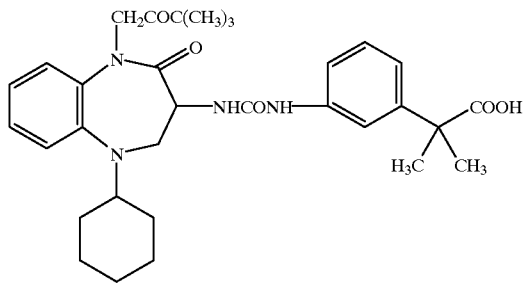

(Step 1)

Preparation of (±)-2-tert-butoxycarbonylamino-3-benzyloxycarbonylaminopropionic acid To an aqueous solution (100 mL) of sodium carbonate (2.05 g), (±)-2-amino-3-benzyloxycarbonylaminopropionic acid (4.6g) prepared in accordance with a known process (Chem. Pharm. Bull., 7, 616 (1959)) was added. A solution of di-tert-butyl dicarbonate (4.68 g) in tetrahydrofuran (100 mL) was then added, followed by stirring overnight at room temperature. The reaction mixture was washed with ethyl acetate. After 1 N hydrochloric acid was added to the aqueous layer to adjust pH to 3, the aqueous layer was extracted with methylene chloride. The organic layer was dried over anhydrous sodium sulfate and the solvent was then evaporated under reduced pressure, whereby the title compound (6.51 g) was obtained.
$^1$H-NMR (CDCl$_3$) δ: 1.43(9H,s),3.45–3.70(2H,m), 4.20–4.42(1H,m), 5.08(2H,s), 5.50(1H,brs), 5.73(1H,brs), 7.32(5H,s), 8.27(1H,brs).
(Step 2)

Preparation of (±)-2-tert-butoxycarbonylamino-3-(2-nitrophenyl)aminopropionic acid (±)-2-tert-Butoxycarbonylamino-3-benzyloxycarbonylam inopropionic acid (1.06 g) was dissolved in methanol (50 mL), followed by the addition of 10% palladium carbon (100 mg). The mixture was stirred at room temperature for 2 hours under a hydrogen atmosphere. The reaction mixture was filtered and the filtrate was concentrated under reduced pressure, whereby (±)-3-amino-2-tert-butoxycarbonylamino-propionic acid (540 mg) was obtained. It was dissolved in ethanol (50 mL). Potassium carbonate (365 mg) and 2-fluoronitrobenzene (377 mg) were then added, followed by refluxing for 3 hours. The reaction mixture was concentrated under reduced pressure, water was added to the residue, and the resultant mixture was washed with diethyl ether. After 1 N hydrochloric acid was added to the aqueous layer to adjust pH to 3, the aqueous layer was extracted with methylene chloride. The organic layer was dried over anhydrous sodium sulfate and the solvent was then evaporated under reduced pressure, whereby the title compound (530 mg) was obtained.
$^1$H-NMR (CDCl$_3$) δ: 1.44(9H,s),3.60–3.95(2H,m), 4.50–4.70(1H,m), 5.37(1H,brs), 6.67–6.73(1H,m), 6.96–7.03(1H,m), 7.43–7.49(1H,m), 8.13–8.19(1H,m), 8.26 (1H,brs), 11.50(1H,brs).
(Step 3)

Preparation of (±)-2-oxo-3-tert-butoxycarbonylamino-1,3,4,5-tetrahydro-2H-1,5-benzodiazepine (±)-2-tert-Butoxycarbonylamino-3-(2-nitrophenyl)-amin opropionic acid (325 mg) was dissolved in methanol (50 mL), followed by the addition of 10% palladium carbon (50 mg). The resulting mixture was stirred at room temperature for 1 hour under a hydrogen atmosphere. The reaction mixture was filtered and the filtrate was concentrated under reduced pressure, whereby (±)-2-tert-butoxycarbonylamino-3-(2-aminophenyl)-aminopropi onic acid was obtained. It was suspended in toluene (30 mL) The suspension was refluxed for 3 hours while removing water by a Dean-Stark extractor. The resultant mixture was concentrated under reduced pressure. After the residue was purified by silica gel colomn chromatography (chloroform:methanol=20:1), diisopropyl ether was added thereto for crystallization. Crystals so precipitated were then collected by filtration, whereby the title compound (210 mg) was obtained. Yield: 76%.
Melting point: 185–187° C.
$^1$H-NMR (CDCl$_3$) δ: 1.44(9H,s),3.39–3.47(1H,m), 3.80–3.98(2H,m), 4.44–4.55(1H,m), 5.73(1H,brs), 6.71–6.88(3H,m), 6.97–7.03(1H,m), 7.82(1H,brs).
(Step 4)

Preparation of (±)-2-oxo-3-tert-butoxycarbonylamino-5-(2-cyclohexen-1-yl)-1,3,4,5-tetrahydro-2H-1,5-benzodiazepine To a solution of (±)-2-oxo-3-tert-butoxycarbonylamino-1,3,4,5-tetrahydro-2H-1,5-benzodiazepine (28.6 g) in N,N-dimethylformamide (50 mL), sodium hydrogencarbonate (17.3 g) and 3-bromocyclohexene (33.2 g) were added, followed by LZ stirring at 50° C. for 1 hour. The reaction mixture was allowed to cool down. Subsequent to addition of ice water, the reaction mixture was extracted with methylene chloride. The organic layer was washed with brine and then dried over anhydrous sodium sulfate. The solvent was evaporated under reduced pressure. Diisopropyl ether was added to the residue for crystallization. Crystals so precipitated were then collected by filtration. The crystals were washed with ethanol and then dried, whereby the title compound (30.1 g) was obtained. Yield: 82%.
$^1$H-NMR (CDCl$_3$) δ: 1.41(9H,s),1.55–2.08(6H,m), 3.23–3.37(1H,m), 3.69–3.82(1H,m), 3.87–4.12(1H,m), 4.42–4.55(1H,m), 5.47–5.54(1H,m), 5.62–6.01(2H,m), 6.90–6.99(2H, m), 7.08–7.22(2H,m) 7.47(1H,brs).
(Step 5)

Preparation of (±)-2-oxo-3-tert-butoxycarbonylamino-5-cyclohexyl-1,3,4,5-tetrahydro-2H-1,5-benzodiazepine To a solution of (±)-2-oxo-3-tert-butoxycarbonylamino-5-(2-cyclohexen-1-yl)-1,3,4,5-tetrahydro-2H-1,5-benzo diazepine (4.5 g) in ethanol (200 mL), 10% palladium carbon (1 g) was added, followed by stirring at room temperature for 2 hours under a hydrogen atmosphere. The reaction mixture was filtered, and the filtrate was concentrated under the reduced pressure. The residue was then recrystallized from ethanol, whereby the title compound (3.35 g) was obtained. Yield: 74%.
Melting point: 207–208° C.
$^1$H-NMR (CDCl$_3$) δ: 1.11–2.07(19H,m), 3.15–3.27(1H,m), 3.33(1H,dd), 3.68(1H,dd), 4.38–4.49(1H,m), 5.53(1H,d), 6.91–6.96(2H,m), 7.11–7.16(2H,m), 7.45(1H,brs).

(Step 6)

Preparation of (±)-1-tert-butylcarbonylmethyl-2-oxo-3-tert-butoxycarbonylamino-5-cyclohexyl-1,3,4,5-tetrahydro-2H-1,5-benzodiazepine To a solution of (±)-2-oxo-3-tert-butoxycarbonylamino-5-cyclohexyl-1,3,4,5-tetrahydro-2H-1,5-benzodiazepine (3.35 g) in dimethyl sulfoxide (30 mL), bromomethyl tert-butyl ketone (2 g), potassium carbonate (1.55 g), potassium iodide (125mg) and tetra (n-butyl) ammonium bromide (120mg) were added, followed by stirring at room temperature for 1 hour. The reaction mixture was poured into ice water, followed by extraction with ethyl acetate. The organic layer was washed with brine and then dried over an hydrous sodium sulfate. The solvent was evaporated under reduced pressure and the residue was purified by silica gel colomn chromatography (ethyl acetate: n-hexane=1:3), whereby the title compound (2.3 g) was obtained.
Melting point: 155–156° C.
$^1$H-NMR (CDCl$_3$) δ: 1.15–2.07(28H,m), 3.13–3.24(1H,m), 3.26(1H,dd), 3.61(1H,dd), 4.11(1H,d), 4.39–4.50(1H,m), 5.17(1H,d), 5.57(1H,d), 6.92–7.03(2H,m), 7.12–7.20(2H,m).

(Step 7)

Preparation of (±)-1-tert-butylcarbonylmethyl-2-oxo-3-amino-5-cyclohexyl-1,3,4,5-tetrahydro-2H-1,5-benzodiazepine To a solution of (±)-1-tert-butylcarbonylmethyl-2-oxo-3-tert-butoxycarbonylamino-5-cyclohexyl-1,3,4,5-tetrahydro-2H-1,5-benzodiazepine (2.2 g) in ethanol (10 mL), 4 N hydrochloric acid-dioxane solution (10 mL) was added. The resulting mixture was stirred at 50° C. for 30 minutes. The reaction mixture was concentrated under reduced pressure, and a saturated aqueous solution of sodium hydrogencarbonate was added to the residue for neutralization. The resultant mixture was extracted with methylene chloride. The organic layer was washed with brine and dried over anhydrous sodium sulfate. The solvent was evaporated under reduced pressure, and diisopropyl ether was added to the residue for crystallization. Crystals so precipitated were collected by filtration, whereby the title compound (1.1 g) was obtained.
Melting point: 124–125° C.
$^1$H-NMR (CDCl$_3$) δ: 1.11–2.08(21H,m), 3.12–3.27(2H,m), 3.40(1H,dd), 3.53–3.62(1H,m), 4.01(1H,d), 5.29(1H,d), 6.92–7.04(2H,m), 7.15–7.19(2H,m).

(Step 8)

Preparation of (±)-1-(1-tert-butylcarbonylmethyl-2-oxo-5-cyclohexyl-1,3,4,5-tetrahydro-2H-1,5-benzodiazepin-3-yl)-3-[3-(1-methyl-1-methoxycarbonyl)ethylphenyl]urea To a solution of methyl 2-(3-aminophenyl)-2-methyl-propionate (142 mg) in dry tetrahydrofuran (50 mL), triphosgene (81.7 mg) was added under ice cooling. Thereafter, triethylamine (335 μL) was added in 5 aliquots, each 67 μL, over 15 minutes. The mixture was stirred at room temperature for 5 minutes. To the mixture, (±)-1-tert-butylcarbonylmethyl-2-oxo-3-amino-5-cyclohexyl-1,3,4,5-tetr ahydro-2H-1,5-benzodiazepine (250 mg) was added under ice cooling. The mixture was stirred to room temperature for 1 hour. Water was added to the reaction mixture, and crystals so precipitated were collected by filtration. The crystals were suspended in methanol, and the suspension so obtained was heated. The suspension was allowed to cool down and the resultant crystals were collected by filtration, whereby the title compound (250 mg) was obtained. Yield: 62%. $^1$H-NMR (DMSO-d$_6$) δ: 1.10–1.82(24H,m), 1.94–2.05(1H,m), 3.16–3.45(3H,m), 3.56(3H,s), 4.30–4.43 (2H,m), 5.12(1H,d), 6.52(1H,d), 6.80–6.85(1H,m), 6.98–7.35(7H,m), 8.87(1H,s).

(Step 9)

Preparation of (±)-2-[3-[3-(1-tert-butylcarbonylmethyl-2-oxo-5-cyclohexyl-1,3,4,5-tetrahydro-2H-1,5-benzodiazepin-3-yl)ureido]phenyl]-2-methylpropionic acid To a solution of (±)-1-(1-tert-butylcarbonylmethyl-2-oxo-5-cyclohexyl-1,3,4, 5-tetrahydro-2H-1,5-benzodiazepin-3-yl)-3-[3-(1-methyl-1-me thoxycarbonyl)ethylphenyl]urea (250 mg) in water-tetrahydrofuran (1:1, 10 mL), lithium hydroxide monohydrate (91 mg) was added, followed by refluxing for 6 hours. The reaction mixture was allowed to cool down. After 1 N hydrochloric acid was added to acidify the reaction mixture, the reaction mixture was extracted with ethyl acetate. The organic layer was washed with brine and then dried over anhydrous sodium sulfate. The solvent was evaporated under reduced pressure, and the residue was purified by silica gel colomn chromatography (chloroform:methanol=10:1). The thus-purified residue was recrystallized from isopropyl alcohol, whereby the title compound (128 mg) was obtained.
Melting point: 215–216° C. (decomposed).
$^1$H-NMR (DMSO-d$_6$) δ: 1.10–1.82(24H,m), 1.94–2.05(1H,m), 3.16–3.45(3H,m), 4.30–4.43(2H,m), 5.12(1H,d), 6.52 (1H,d), 6.84–6.88(1H,m), 6.98–7.39(7H,m), 8.85(1H,s), 12.20(1H,brs).
MS (FAB) m/z: 563 (MH$^+$).

Example 2

Preparation of (R)-(-)-2-[3-[3-(1-tert-butylcarbonylmethyl-2-oxo-5-cyclohexyl-1,3,4,5-tetrahydro-2H-1,5-benzodi azepin-3-yl)ureido]phenyl]-2-methylpropionic acid

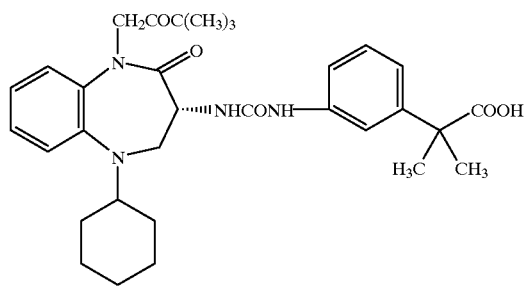

(Step 1)

Preparation of (R)-(-)-2-tert-butoxycarbonylamino-3-(2-nitrophenylamino)propionic acid To a solution of 2-fluoronitrobenzene (3.45 g) in N,N-dimethylformamide (60 mL), (R)-(-)-2-tert-butoxycarbonylamino-3-amino-propionic acid (5 g) and potassium carbonate (6.77 g) were added, followed by stirring overnight at 70° C. The reaction mixture was allowed to cool down, poured into ice water, and then extracted with ethyl acetate. After 1 N hydrochloric acid was added to the aqueous layer to adjust pH to 3, the aqueous layer was extracted with ethyl acetate. The organic layer was washed with brine and dried over anhydrous sodium sulfate. The solvent was then evaporated under reduced pressure. n-Hexane was added to the residue to for crystallization. The resultant crystals were collected by filtration, whereby the title compound (7.9 g) was obtained. Yield: 99%.

Melting point: 141–142° C. (decomposed).
[α]D$^{25}$(C=1.00, CHCl$_3$): –145°.
(Step 2)
Preparation of (R)-(+)-2-oxo-3-tert-butoxycarbonylamino-1,3,4,5-tetrahydro-2H-1,5-benzodiazepine To a solution of (R)-(–)-2-tert-butoxycarbonylamino-3-(2-nitrophenylamino)propionic acid (7.6 g) in tetrahydrofuran (100mL), 10% palladium carbon (1 g) was added, followed by stirring at room temperature for 3 hours under a hydrogen atmosphere. The reaction mixture was filtered and the filtrate was concentrated under reduced pressure, whereby (R)-2-tert-butoxycarbonylamino-3-(2-aminophenylamino)-propi onic acid was obtained. It was dissolved in toluene (100 mL). The solution was refluxed overnight. The reaction mixture was allowed to cool down and then concentrated under reduced pressure. The residue was purified by silica gel colomn chromatography (ethyl acetate:n-hexane=1:1), whereby the title compound (5.16 g) was obtained. Yield: 80%.
Melting point: 158–160° C.
[α]D$^{25}$(C=1.01, CHCl$_3$): +7.21°.
Optical purity: 98%ee (measured by liquid chromatography).
(Step 3)
Preparation of (3R)-(–)-2-oxo-3-tert-butoxycarbonylamino-5-(2-cyclohexen-1-yl)-1,3,4,5-tetrahydro-2H-1,5-benzodiazepine To a solution of (R)-(+)-2-oxo-3-tert-butoxycarbonylamino-1,3,4,5-tetrahydro-2H-1,5-benzodiazepine (6.08g) in dry N,N-dimethylformamide (50 mL), sodium hydrogencarbonate (3.68 g) and 3-bromocyclohexene (7.06 g) were added, followed by stirring at 50° C. for 1 hour. The reaction mixture was allowed to cool down, and subsequent to addition of ice water, was extracted with ethyl acetate. The organic layer was washed with brine and dried over anhydrous sodium sulfate, and the solvent was then evaporated under reduced pressure. The residue was purified by silica gel column chromatgraphy (ethyl acetate:n-hexane=1:3), whereby the title compound (7.84 g) was obtained.
[α]D$^{25}$ (C=1.00, CHCl$_3$): –179°.
(Step 4)
Preparation of (R)-(–)-2-oxo-3-tert-butoxycarbonylamino-5-cyclohexyl-1,3,4,5-tetrahydro-2H-1,5-benzodiazepine To a solution of (3R)-(–)-2-oxo-3-tert-butoxycarbonylamino-5-(2-cyclohexen-1-yl)-1,3,4,5-tetrahydro-2H-1 ,5-benzodiazepine (7.7g) in tetrahydrofuran (200 mL), platinum oxide (200 mg) was added subsequent to pre-reduction. The resulting mixture was stirred at room temperature for 2 hour under a hydrogen atmosphere. The reaction mixture was filtered through Celite, and the filtrate was concentrated under reduced pressure. The residue was purified by silica gel column chromatography(ethyl acetate:n-hexane=1:3). Diisopropyl ether was added to the residue for crystallization the same. Crystals so precipitated were collected by filtration, whereby the title compound (5.16 g) was obtained. Yield: 67%.
[α]D$^{23}$ (C=1.00, CHCl$_3$): –184°.
(Step 5)
Preparation of (R)-(–)-2-oxo-3-amino-5-cyclohexyl-1,3,4,5-tetrahydro-2H-1,5-benzodiazepine To a solution of (R)-(–)-2-oxo-3-tert-butoxycarbonylamino-5-cyclohexyl-1,3,4,5-tetrahydro-2H-1,5-benzodiazepine (5.11 g) in ethanol (15 mL), 4 N hydrochloric acid-dioxane solution (10 mL) was added. The mixture was stirred at 50° C. for 1 hour. The reaction mixture was allowed to cool down and then concentrated under reduced pressure. A saturated aqueous solution of sodium hydrogencarbonate was added to the residue for neutralization. The resultant mixture was extracted with chloroform. The organic layer was washed with brine and dried over anhydrous sodium sulfate. The solvent was evaporated under reduced pressure. Crystals so precipitated were washed with diisopropyl ether and then collected by filtration. The crystals were recrystallized from a mixed solvent of ethanol and diisopropyl ether, whereby the title compound (2.1 g) was obtained.
Melting point: 180–182° C.
$^1$H-NMR (CDCl$_3$) 67 : 1.06–2.07(12H,m), 3.17–3.32(2H, m), 3.49–3.62(2H,m), 6.90–6.99(2H,m), 7.09–7.18(2H,m), 7.45(1H,s).
[α]D$^{25}$(C=1.04, CHCl$_3$): –163°.
Optical purity: 99%ee or higher (measured by liquid chromatography).
(Step 6)
Preparation of (R)-(–)-1-(2-oxo-5-cyclohexyl-1,3,4,5-tetrahydro-2H-1,5-benzodiazepin-3-yl)-3-[3-(1-methyl-1-tert -butoxycarbonyl)ethylphenyl]urea To a solution of tert-butyl 2-(3-aminophenyl)-2-methylpropionate (1.88 g) in dry tetrahydrofuran (100 mL), triphosgene (890 mg) was added under ice cooling. Thereafter, triethylamine (3.45 mL) was added in 5 aliquots, each 690 μL, over 15 minutes. The mixture was stirred for 5 minutes at room temperature. To the resultant mixture, (R)-(–)-2-oxo-3-amino-5-cyclohexyl-1,3,4,5-tetrahydro-2H-1,5-benzodiazepine (2.0 g) was added under ice cooling. The thus-obtained mixture was stirred at room temperature for 1 hour. The reaction mixture was concentrated under reduced pressure. Water was added to the residue, followed by extraction with methylene chloride. The organic layer was washed with brine and dried over anhydrous sodium sulfate. The solvent was then evaporated under reduced pressure. The residue was recrystallized from acetonitrile, whereby the title compound (2.64 g) was obtained. Yield: 64%.
Melting point: 185–187° C.
[α]D$^{23}$(C=1.03, CHCl$_3$): –159°.
(Step 7)
Preparation of (R)-(–)-1-(1-tert-butylcarbonylmethyl-2-oxo-5-cyclohexyl-1 3,4,5-tetrahydro-2H-1,5-benzodiazepin-3-yl)-3-[3-(1-methyl-1-tert-butoxycarbonyl)ethylphenyl]urea To a solution of (R)-(–)-1-(2-oxo-5-cyclohexyl-1,3,4,5-tetrahydro-2H-1,5-benzodiazepin-3-yl)-3-[3-(1-methy l-1-tert-butoxycarbonyl)ethylphenyl]urea (2.6 g) in dimethyl sulfoxide (50 mL), bromomethyl tert-butyl ketone (1.34 g), potassium carbonate (1.04 g), potassium iodide (62 mg) and tetra(n-butyl)ammonium bromide (73 mg) were added, and the mixture was stirred at room temperature for 2 hours. Ice water was added to the reaction mixture, followed by extraction with ethyl acetate. The organic layer was washed with brine and dried over anhydrous sodium sulfate. The solvent was evaporated under reduced pressure and the residue was purified by silica gel column chromatography (ethyl acetate:n-hexane=1:2), whereby the title compound (2.8 g) was obtained. Yield: 90%.
Melting point: 159–161° C.
[α]D$^{21}$(C=1.2, CHCl$_3$) : –69°.
(Step 8)
Preparation of (R)-(–)-2-[3-[3-(1-tert-butylcarbonylmethyl-2-oxo-5-cyclohexyl-1,3,4,5-tetrahydro-2H-1,5-benzodi azepin-3-yl)ureido]phenyl]-2-methylpropionic acid To a solution of (R)-(−)-1-(1-tert-butylcarbonylmethyl-2-oxo-5-cyclohexyl-1,3,4,5-tetrahydro-2H-1,5-benzodiazepin-3-yl)-3-[3-(1-methyl-1-tert-butoxycarbonyl)-ethylphenyl]urea (2.6 g) in methylene chloride (10 mL), trifluoroacetic acid (10 mL) was added, followed by stirring at room temperature for 1 hour. The reaction mixture was concentrated under reduced pressure, and diisopropyl ether was added to the residue for crystallization. Crystals so precipitated were collected by filtration, whereby the title compound (960 mg) was obtained.
Melting point: 139–144° C.
$[\alpha]_D^{23}$(C=1.03, CHCl$_3$): −111°.

Example 3

Preparation of (R)-2-[3-[3-(1-tert-butylcarbonylmethyl-2-oxo-5-cyclohexyl-1,3,4,5-tetrahydro-2H-1,5-benzodiazepin-3-yl)ureido]phenyl]-2-methylpropionic acid trans-4-aminocyclohexanol salt

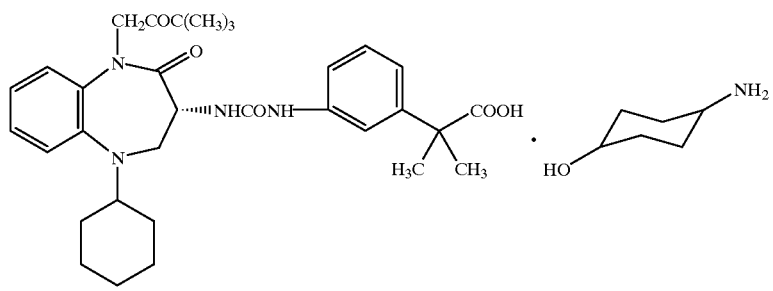

(R)-(−)-2-[3-[3-(1-tert-Butylcarbonylmethyl-2-oxo-5-cyclohexyl-1,3,4,5-tetrahydro-2H-1,5-benzodiazepin-3-yl)ureido]phenyl]-2-methylpropionic acid (42 mg) was dissolved in acetonitrile (0.5 mL). Trans-4-amino-cyclohexanol (8 mg) was added and then dissolved under heat. After the mixture was allowed to stand overnight, crystals so precipitated were collected by filtration and dried, whereby the title compound (39 mg) was obtained. Yield: 77%.
Melting point: 180–182° C.
$^1$H-NMR (DMSO-d$_6$) 67 : 1.09–1.97(22H,m), 1.17(9H,s), 1.35(6H,s), 2.63(1H,m), 3.18–3.42(5H,m), 4.34(2H,m), 5.11(1H,d), 6.64(1H,d), 6.86–7.31(8H,m),8.95(1H,s).

Example 4

Preparation of (R)-2-[3-[3-(1-tert-butylcarbonylmethyl-2-oxo-5-cyclohexyl-1,3,4,5-tetrahydro-2H-1,5-benzodiazepin-3-yl)ureido]phenyl]-2-methylpropionic acid N,N'-dibenzylethylenediamine salt

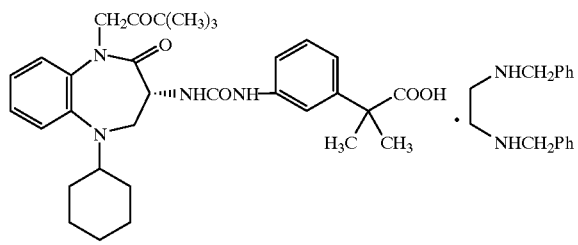

(R)-(−)-2-[3-[3-(1-tert-Butylcarbonylmethyl-2-oxo-5-cyclohexyl-1,3,4,5-tetrahydro-2H-1,5-benzodiazepin-3-yl)ureido]phenyl]-2-methylpropionic acid (158 mg) and N,N'-dibenzylethylenediamine (67 mg) were added to acetonitrile (2 mL), and were then dissolved under heat. The reaction mixture was allowed to stand. Crystals so precipitated were collected by filtration and dried, whereby the title compound (200 mg) was obtained. Yield: 89%.

Melting point: 105–106° C.

$^1$H-NMR (DMSO-d$_6$) 67 : 1.17(9H,s), 1.20–1.99(10H,m), 1.40(6H,s), 2.58(4H,s), 3.17–3.44(5H,m), 3.67(4H,s), 4.34–4.43(2H,m), 5.12(1H,d), 6.53(1H,d), 6.87–7.37(18H,m), 8.87(1H,s).

Example 5

Preparation of sodium (R)-2-[3-[3-(1-tert-butylcarbonylmethyl-2-oxo-5-cyclohexyl-1,3,4,5-tetrahydro-2H-1,5-benzodiazepin-3-yl)ureido]phenyl]-2-methylpropionate

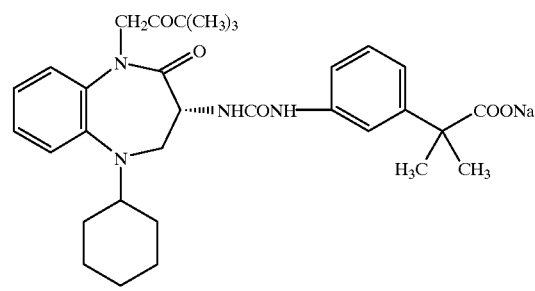

To a solution of (R)-(−)-2-[3-[3-(1-tert-butylcarbonylmethyl-2-oxo-5-cyclohexyl-1,3,4,5-tetrahydro-2H-1,5-benzodiazepin-3-yl)ureido]phenyl]-2-methylpropionic acid (960 mg) in methanol (10 mL), 1 N sodium hydroxide (1.79 mL) was added. The solution was concentrated under reduced pressure. The residue was purified through HP-20 ("Diaion", product of Mitsubishi Chemical Corporation) by means of water and methanol. The thus-purified residue was lyophilized, whereby the title compound (900 mg) was obtained.
$^1$H-NMR (DMSO-d$_6$) δ: 1.10–1.83(24H,m), 1.90–2.05(1H, m), 3.15–3.50(3H,m), 4.34–4.43(2H,m), 5.09(1H,d), 6.85–6.95(2H,m),6.97–7.12(3H,m), 7.20–7.30(4H,m), 9.20 (1H,s).

Example 6

Preparation of (R)-(−)-2-[3-[3-(1-tert-butylcarbonylmethyl-2-oxo-5-phenyl-1,3,4,5-tetrahydro-2H-1,5-benzo-diazepin-3-yl)ureido]phenyl]-2-methylpropionic acid

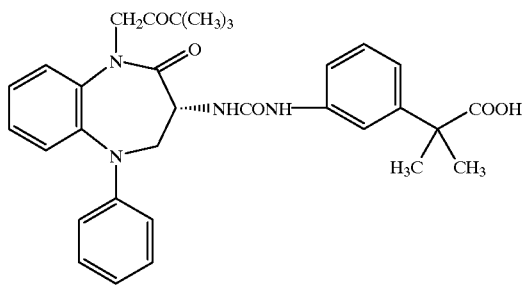

(Step 1)
Preparation of (3R)-(−)-2-oxo-3-amino-5-phenyl-1,3,4,5-tetrahydro-2H-1,5-benzodiazepine To a solution of (3R)-2-oxo-3-butoxycarbonylamino-5-(2-cyclohexen-1-yl)-1,3,4,5-tetrahydro-2H-1,5-benzodiazepine (12.87 g) in xylene (200 mL), nitrobenzene (22.16 g) and 10% palladium carbon (6 g) were added, followed by refluxing for 1 hour and 30 minutes. The reaction mixture was allowed to cool down and then filtered. The filtrate was concentrated under reduced pressure. The residue was dissolved in ethanol (30mL), and a 4 N hydrochloric acid-dioxane solution (20 mL) was added, followed by stirring at 50° C. for 1 hour. After the reaction mixture was allowed to cool down, crystals so precipitated were collected by filtration and washed with 2-propanol, whereby the hydrochloride of the title compound was obtained. The hydrochloride was then dissolved under heat in a mixed solution of methanol and water. After the reaction mixture was allowed to cool down, a saturated aqueous solution of sodium hydrogencarbonate was added to the reaction mixture for neutralization. Crystals so precipitated were collected by filtration, washed with water and then dried, whereby the title compound (5.55 g) was obtained.
$^1$H-NMR (DMSO-d$_6$) δ: 1.83(2H,brs), 3.41–3.53(2H,m), 3.89(1H,ABq), 6.62–6.68(2H,m),6.74–6.81(1H,m), 7.08–7.25(6H,m), 9.87(1H,s).
$[α]_D^{23}$(C=1.00, DMSO): −66.0°.

(Step 2)
Preparation of (R)-(−)-1-(2-oxo-5-phenyl-1,3,4,5-tetrahydro-2H-1,5-benzodiazepin-3-yl)-3-[3-(1-methyl-1-tert-butoxycarbonyl)ethylphenyl]urea Under ice cooling, triphosgene (445 mg) was added to and mixed with a solution of tert-butyl 2-(3-aminophenyl)-2-methylpropionate (941 mg) in dry tetrahydrofuran (100 mL). Thereafter, triethylamine (1.7 mL) was added in 5 aliquots, each 0.34 mL, over 15 minutes. The mixture was stirred at room temperature for 5 minutes. To the resultant mixture, (R)-(−)-2-oxo-3-amino-5-phenyl-1,3, 4,5-tetrahydro-2H-1,5-benzodiazepine (1 g) was added under ice cooling. The thus-obtained mixture was stirred at for 1 hour. The reaction mixture was concentrated under reduced pressure. Water was added to the residue, followed by extraction with ethyl acetate. The organic layer was washed with brine and dried over anhydrous sodium sulfate. The solvent was then evaporated under reduced pressure. Acetonitrile was added to the residue for crystallization. Crystals so precipitated were collected by filtration whereby the title compound (850 mg) was obtained.
Melting point: 166–168° C. (decomposed).
$^1$H-NMR (CDCl$_3$) δ: 1.32(9H,s), 1.50(3H,s), 1.53(3H,s), 3.74(1H,dd), 4.44(1H,dd), 4.97(1H,dt), 6.22(1H,d), 6.72–6.98(4H,m), 7.14–7.33(8H,m), 7.67–7.71(1H,m), 8.30 (1H,s), 8.43(1H,s).
$[α]_D^{21}$(C=1.00, CHCl$_3$): −191°.

(Step 3)
Preparation of (R)-(−)-1-(1-tert-butylcarbonylmethyl-2-oxo-5-phenyl-1,3,4,5-tetrahydro-2H-1,5-benzodiazepin-3-yl )-3-[3-(1-methyl-1-tert-butoxycarbonyl)ethylphenyl]urea Under ice cooling, (R)-(−)-1-(2-oxo-5-phenyl-1,3,4,5-tetrahydro-2H-1,5-benzodiazepin-3-yl)-3-[3-(1-methyl-1-tert -butoxycarbonyl)ethylphenyl]urea (800 mg) was added to a solution of 60% sodium hydride (75 mg) in dry N,N-dimethylformamide (20 mL), and after stirring for 1 hour, chloromethyl tert-butyl ketone (251 mg) was added, followed by stirring for 1 hour. After allowed to room temperature, the mixture was stirred for 30 minutes. Ice water was added to the reaction mixture, followed by extraction with ethyl acetate. The organic layer was washed with brine and dried over anhydrous sodium sulfate, and the solvent was then evaporated under reduced pressure. The residue was purified by silica gel column chromatography (ethyl acetate:n-hexane=1:2), whereby the title compound (920 mg) was obtained. Yield: 97%.
$^1$H-NMR (CDCl$_3$) δ: 1.23(9H,s), 1.36(9H,s), 1.48(6H,s), 3.65(1H,dd), 4.26(1H,dd), 4.39(1H,d), 4.90(1H,dt), 5.14 (1H,d), 6.77–6.89(4H,m), 6.95–7.00(1H,m), 7.10–7.33 (10H,m).
$[α]_D^{21}$(C=1.02, CHCl$_3$): −108°.

(Step 4)
Preparation of (R)-(−)-2-[3-[3-(1-tert-butylcarbonylmethyl-2-oxo-5-phenyl-1,3,4,5-tetrahydro-2H-1,5-benzodiazepin-3-yl)ureido]phenyl]-2-methylpropionic acid Concentrated hydrochloric acid (2 mL) was added to a solution of (R)-(−)-1-(1-tert-butylcarbonylmethyl-2-oxo-5-phenyl-1,3,4, 5-tetrahydro-2H-1,5-benzodiazepin-3-yl)-3-[3-(1-methyl-1-te rt-butoxycarbonyl)ethylphenyl] urea (850mg) in acetone (10 mL), followed by stirring at 50° C. for 1 hour. The reaction mixture was concentrated under reduced pressure, and water was added to the residue. The thus-obtained mixture was extracted with ethyl acetate. The extract was washed with brine and dried over anhydrous sodium sulfate, and the solvent was then evaporated under reduced pressure. The residue was purified by silica gel column chromatography (chloroform: methanol=10:1), whereby the title compound (760 mg) was obtained. Yield: 98%.
$^1$H-NMR (DMSO-d$_6$) δ: 1.17(9H,s), 1.42(6H,s), 3.57(1H, dd), 3.97–4.07(2H,m), 4.58(1H,dt), 4.79(1H,d), 5.12(1H,d), 6.63(1H,d), 6.78–6.92(4H,m), 7.13–7.33(8H,m), 7.42(1H, s), 8.94(1H,s), 12.25(1H,brs).
$[α]_D^{25}$(C=1.01, CHCl$_3$): −160 °.

Referential Preparation Example 1
Preparation of methyl 2-(3-aminophenyl)-2-methyl-propionate
(Step 1)
Through a solution of 3-nitrophenylacetonitrile (2 g) in methanol (50 mL), hydrogen chloride gas was bubbled under ice cooling until saturation. After the solution was stirred at room temperature for 1 hour, water (0.4 mL) was added, followed by refluxing for 1 hour. The reaction mixture was allowed to cool down and then concentrated under reduced pressure. A saturated aqueous solution of sodium hydrogencarbonate was added to the residue for neutralization, followed by extraction with ethyl acetate. The organic layer was washed with brine and dried over anhydrous sodium sulfate. The solvent was evaporated under reduced pressure, whereby methyl 3-nitrophenylacetate (2.31 g) was obtained.
$^1$H-NMR (CDCl$_3$) δ: 3.73(3H,s), 3.75(2H,s), 7.48–7.55(1H, m), 7.61–7.65(1H,m), 8.10–8.19(2H,m).

(Step 2)

Under ice cooling, a solution of methyl 3-nitrophenylacetate (2.3g) in N,N-dimethylformamide (10 mL) was added dropwise to a suspension of 60% sodium hydride (1.04 g) in dry N,N-dimethylformamide (50 mL), and after stirring for 10 minutes, methyl iodide (1.62 mL) was added dropwise. The mixture was stirred at room temperature for 2 hours. Ice water was added to the reaction mixture, followed by extraction with ethyl acetate. The organic layer was washed with brine and dried over anhydrous sodium sulfate, and the solvent was then evaporated under reduced pressure. The residue was purified by silica gel column chromatography (ethyl acetate: n-hexane=1:5), whereby methyl 2-(3-nitrophenyl)-2-methylpropionate (1.8 g) was obtained.

$^1$H-NMR (CDCl$_3$) δ: 1.65(6H,s), 3.68(3H,s), 7.47–7.55(1H, m), 7.65–7.70(1H,m), 8.10–8.15(1H,m), 8.22–8.25(1H,m).

(Step 3)

To a solution of methyl 2-(3-nitrophenyl)-2-methylpropionate (1.8 g) in methanol (50 mL), 10% palladium carbon (200 mg) was added, followed by stirring at room temperature for 2 hours under a hydrogen atmosphere. The reaction mixture was filtered, and the filtrate was concentrated under reduced pressure. The residue was purified by silica gel column chromatography (ethyl acetate: n-hexane=1:2), whereby methyl 2-(3-aminophenyl)-2-methyl-propionate (1.5 g) was obtained.

$^1$H-NMR (CDCl$_3$) δ: 1.54(6H,s), 3.65(3H,s), 3.70(2H,brs), 6.54–6.59(1H,m), 6.63–6.67(1H,m), 6.70–6.75(1H,m), 7.11 (1H,t).

Referential Preparation Example 2

Preparation of tert-butyl 2-(3-aminophenyl)-2-methylpropionate (Step 1)

To a solution of 3-nitrophenylacetic acid (2.9 g) in tert-butyl alcohol-tetrahydrofuran (1:1, 40 mL), di(tert-butyl) dicarbonate (5.24 g) and 4-dimethylaminopyridine (0.5g) were added, followed by stirring at room temperature until bubbling stopped. The reaction mixture was concentrated under reduced pressure, and ethyl acetate was added to the residue for extraction. The extract was washed successively with a 10% aqueous solution of citric acid, a saturated aqueous solution of sodium hydrogencarbonate, water and brine, and was then dried over anhydrous sodium sulfate. The solvent was distilled off under reduced pressure, whereby tert-butyl 3-nitrophenyl-acetate (3.8 g) was obtained.

$^1$H-NMR (CDCl$_3$) δ: 1.46(9H,s), 3.65(3H,s), 7.47–7.54(1H, m), 7.59–7.64(1H,m), 8.11–8.17(2H,m).

(Step 2)

Under ice cooling, a solution of tert-butyl 3-nitrophenylacetate (3.8 g) in dry N,N-dimethylformamide (10 mL) was added dropwise to a suspension of 60% sodium hydride (1.41g) in dry N,N-dimethylformamide (50mL), and after stirring for 10 minutes, methyl iodide (2.2 mL) was added dropwise. The mixture was stirred at room temperature for 2 hours. Ice water was added to the reaction mixture, followed by extraction with ethyl acetate. The organic layer was washed with brine and dried over anhydrous sodium sulfate, and the solvent was then evaporated under reduced pressure. The residue was purified by silica gel column chromatography (ethyl acetate: n-hexane=1:5), whereby tert-butyl 2-(3-nitro-phenyl)-2-methylpropionate (3.6 g) was obtained.

$^1$H-NMR (CDCl$_3$) δ: 1.39(9H,s), 1.59(6H,s), 7.45–7.53(1H, m), 7.64–7.71(1H,m), 8.08–8.14(1H,m), 8.22–8.26(1H,m).

(Step 3)

To a solution of t-butyl 2-(3-nitrophenyl)-2-methylpropionate (3.6 g) in ethanol (100 mL), 10% palladium carbon (400 mg) was added, followed by stirring at room temperature for 2 hours under a hydrogen atmosphere. The reaction mixture was filtered, and the filtrate was concentrated under reduced pressure. The residue was purified by silica gel column chromatography (ethyl acetate: n-hexane= 1:5), whereby tert-butyl 2-(3-aminophenyl)-2-methylpropionate (2.87 g) was obtained.

$^1$H-NMR (CDCl$_3$) δ: 1.38(9H,s), 1.48(6H,s), 3.62(2H,brs), 6.52–6.57(1H,m), 6.65–6.68(1H,m), 6.71–6.76(1H,m), 7.09 (1H,t).

Test 1

<CCK-B Receptor Binding Test>

From a male Hartley strain guinea pig, the cerebral cortex was removed. After the cerebral cortex was homogenized with 50 mM tris-HCl buffer (pH 7.4) in an amount 50 times as much as the weight of the cerebral cortex, the homogenate was centrifuged under 50,000 g for 10 minutes. With respect to the resulting pellet, addition of the same buffer in the same amount and centrifugation were repeated twice. The finally-obtained pellet was homogenized with 10 mM HEPES buffer (pH 6.5, hereinafter called "the solvent") which contained magnesium chloride (5mM), EGTA (1mM), bacitracin (0.25mg/mL) and sodium chloride (130 mM), and the homogenate was provided as a receptor sample.

As a binding experiment, a [$^3$H]CCK-B solution of a final concentration of 1.0 nM (50 μL) and the receptor sample (protein content: 800 μg/tube) (900 μL) were added to the solvent, the CCK-B solution of a final concentration of 1.0 μM or a test compound solution (50 μL), followed by a reaction at 25° C. for 2 hours. After completion of the reaction, the reaction mixture was filtered by suction through a Wattman GF/B Filter which had been treated with 0.1% BSA, and the filter was immediately washed four times with 3 mL portions of ice-chilled 50 mM tris-HCl buffer (pH 7.4). ACS-II scintillator was added to the filter and, after the filter was left over for 24 hours, the radioactivity concentration on the filter was measured by a liquid scintillation counter. A binding in the presence of CCK-B (1 μM) was recorded as a non-specific binding, while a value obtained by subtracting the non-specific binding from a full binding, which had been obtained using the solvent instead of CCK-B, was recorded as a specific binding. From the specific binding of [$^3$H]CCK-B, the binding inhibition constant (Ki value) of the compound was calculated. As a result, the Ki value of the compound of Example 2 was determined to be 0.74nM.

Test 2

<Inhibition Test on Pentagastrin-stimulated Acid Secretion in Rats>

Male Sprague-Dawley (SD) strain rats were used. Under anesthesia with ethyl ether, operations were performed on each rat to ligate the gastric antrum and also to arrange an intraduodenal catheter and a gastric fistula tube. After completion of the operations, the rat was placed in a Ballmann cage, and pentagastrin was continuously injected at 15 μg/kg/hr through the caudal vein. Each test compound was formed into a suspension by using a 0.5% carboxymethylcellulose sodium solution (hereinafter called "the solvent"). Upon an elapsed timeof 1 hour from the initiation of the injection of pentagastrin, the solvent or the test compound was administered through the intraduodenal catheter. The acidity of sampled gastric juice was measured using an autotitrater, and a product of the acidity and the amount of the gastric juice was recorded as an acid output.

Based on acid output over 3 hours ranging from the $1^{st}$ hour to the $4^{th}$ hour after the administration of the test compound, an acid output inhibition rate was determined using the below-described formula. As a result, the compound of Example 2 exhibited an acid secretion inhibition of 72.7% when administered at 0.3 mg/kg, and the compound of Example 5 showed acid secretion inhibitions of 48.4% and 79.3% when administered at 0.1 mg/kg and 0.3 mg/kg, respectively.

$$\text{Inhibition rate }(\%) = \frac{\substack{\text{Average of acid} \\ \text{output in the solvent-} \\ \text{administered group}} - \substack{\text{Average of acid} \\ \text{output in the compound-} \\ \text{administered group}}}{\text{Average of acid output in the solvent-administered group}} \times 100$$

Test 3
<CCK-A Receptor Binding Test>

From a male Hartley strain guinea pig, the pancreas was removed. The pancreas was homogenized with 10 mM PIPES buffer (pH 6.5, hereinafter called "the solvent") in an amount 40 times as much as the weight of the pancreas. The solvent contained EGTA (1 mM), magnesium chloride (30 mM), bacitracin (0. 02%), soybean trypsin inhibitor (0.02%), and sucrose (0.3 M). After filtered through gauze, the homogenate was centrifuged under 50,000 g for 10 minutes. To the resulting pellet, the solvent was added again in an amount as much as the pellet, followed by centrifugation. To the thus-obtained pellet the solvent was added in an amount 40 times as much as the pellet, and the pellet was homogenized. The homogenate was provided as a receptor sample.

As a binding experiment, a solution (50 µL) of [$^3$H]L-364,718 (devazepide), said solution having a final concentration of 0.2 nM, and the receptor sample (protein content: 50 µg/tube) (900 µL) were added to the solvent, an L-364,718 solution of a final concentration of 1 µM or a test compound solution (50 µL), followed by a reaction at 25° C. for 2 hours. After completion of the reaction, the reaction mixture was filtered by suction through a Wattman GF/B Filter which had been treated with 0.1% BSA (bovine serum albumin), and the filter was immediately washed three times with 3mL portions of ice-chilled 10 mM PIPES buffer (pH 6.5). ACS-II scintillator was added to the filter and, after the filter was left over for 24 hours, the radioactivity concentration on the filter was measured by a liquid scintillation counter. A binding in the presence of L-364,718 (1 µM) was recorded as a non-specific binding, while a value obtained by subtracting the non-specific binding from a full binding, which had been obtained using the solvent instead of L-364,718, (1 µM) was recorded as a specific binding. From the specific binding of [$^3$H]L-364,718, the binding inhibition constant (Ki value) of the compound was calculated. As a result, the Ki value of the compound of Example 2 was determined to be 438 nM.

Test 4
<Inhibition Test on Pentagastrin-stimulated Acid Secretion in Beagles with Heidenhain Pouch>

Male beagles with Heidenhain pouch formed beforehand were used. Pentagastrin was continuously and intravenously injected at 4 µg/kg/hr. Upon an elapsed time of 3 hours after the initiation of the continuous injection of pentagastrin, each test compound was filled in gelatin capsules and orally administered. The acidity of sampled gastric juice was measured using an autotitrater, and a product of the acidity and the amount of the gastric juice was recorded as an acid output. Supposing -that an acid output during 1 hour preceding the administration was 100%, acid output over 3 hours ranging from the $1^{st}$ hour to the $4^{th}$ hour after the administration of the test compound were converted into percentages (acid output percentages). Based on such acid output percentages, the acid output inhibition rate of each beagle was determined using the below-described formula. An average of such acid output inhibition rates was recorded as the acid inhibition rate of the compound. As a result, the compound of Example 2 exhibited an acid secretion inhibition of 77.9% when administered at 1 mg/kg.

$$\text{Inhibition rate }(\%) = \frac{\substack{\text{Acid output percentage under} \\ \text{conditions of control}} - \substack{\text{Acid output percentage after} \\ \text{administration of test compound}}}{\text{Acid output percentage under conditions of control}} \times 100$$

Pharmaceutical Preparation Example 1

| | |
|---|---|
| Compound of Example 5 | 20 g |
| Lactose | 315 g |
| Corn starch | 125 g |
| Crystalline cellulose | 25 g |

The above-described ingredients were uniformly mixed. A 7.5% aqueous solution of hydroxy-propylcellulose (200 mL) was then added. By an extruder equipped with a screen of 0.5 mm in diameter, the mass so prepared was formed into granular pieces. The granular pieces were immediately rounded by a Marumerizer and then dried, wehreby granules were obtained.

Pharmaceutical Preparation Example 2

| | |
|---|---|
| Compound of Example 2 | 20 g |
| Lactose | 100 g |
| Corn starch | 36 g |
| Crystalline cellulose | 30 g |
| Carboxymethylcellulose calcium | 10 g |
| Magnesium stearate | 4 g |

The above-described ingredients were uniformly mixed. On a single-punch tableting machine, the mixture was formed into tablets of 200 mg per tablet by a punch of 7.5 mm in diameter.

Pharmaceutical Preparation Example 3

| | |
|---|---|
| Compound of Example 6 | 100 mg |
| Sodium acetate | 2 mg |
| Acetic acid (for adjustment to pH 5.8) | q.s. |
| Distilled water | q.s. |
| Total | 10 mL/bial |

According to the above formula, an injection was prepared in a manner known per se in the art.

Industrial Applicability

The compounds of the present invention have strong gastrin receptor and/or CCK-B receptor antagonism and strong acid secretion inhibiting effect and also are high in safety. Accordingly, they can be used extensively in the field of medical treatment for treating, improving and/or preventing diseases in which gastrin receptors and/or CCK-B receptors take part, for example, gastric ulcer, duodenal ulcer, gastritis, reflux esophagitis, pancreatitis, Zollinger-Ellison syndrome, vacuolating G cell hyperplasia, basal mucosa hyperplasia, cholecystitis, biliary colic, gastrointestinal dysmotility, irritable bowel syndrome, certain types of tumors, eating disorder, anxiety, panic disorder, depression, schizophrenia, parkinsonism, tardive dyskinesia, Gilles de la Tourette's syndrome, drug dependence, and drug-withdrawal symptoms, and also for inducing ataralgesia and enhancing ataralgesia induction by opioid drugs.

What is claimed is:

1. A compound of formula (1):

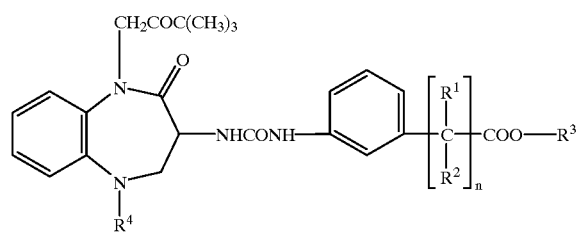

(1)

wherein $R^1$ represents a lower alkyl group, $R^2$ and $R^3$ may be the same or different and represent a hydrogen atom or a lower alkyl group, $R^4$ represents a cyclohexyl group or phenyl group, and n stands for an integer of from 1 to 3; or a salt thereof.

2. A compound according to claim 1, wherein $R^1$ and $R^2$ are methyl groups, $R^3$ is a hydrogen atom, and n is 1.

3. A pharmaceutical composition comprising a compound according to claim 1 or 2 and a pharmaceutically acceptable carrier.

4. A treatment method of a disease in which a gastrin receptor and/or a CCK-B receptor takes part, wherein said disease is a disease selected from eating disorder, anxiety, panic disorder, depression, schizophrenia, tardive dyskinesia, Gilles de la Tourette's syndrome, gastric ulcer, duodenal ulcer, gastritis, reflux esophagitis or Zollinger-Ellison syndrome, which comprises administering to a subject an amount effective therefor of a compound according to claim 1 or 2.

* * * * *

UNITED STATES PATENT AND TRADEMARK OFFICE
CERTIFICATE OF CORRECTION

PATENT NO. : 6,344,452 B1
DATED : February 5, 2002
INVENTOR(S) : Shinozaki et al.

It is certified that error appears in the above-identified patent and that said Letters Patent is hereby corrected as shown below:

<u>Title page,</u>
Item [73], the Assignee's information should read:

-- [73] Assignee: Zeria Pharmaceutical Co., Ltd.,
Tokyo (JP) --

Item [22], the PCT Filing Date should read:

-- [22] PCT Filed: May 28, 1999 --

Signed and Sealed this

First Day of October, 2002

Attest:

Attesting Officer

JAMES E. ROGAN
*Director of the United States Patent and Trademark Office*